United States Patent [19]
DeLuca et al.

[11] Patent Number: 5,716,946
[45] Date of Patent: Feb. 10, 1998

[54] MULTIPLE SCLEROSIS TREATMENT

[75] Inventors: Hector F. DeLuca, Deerfield; Colleen E. Hayes, Madison; Margherita T. Cantorna, Middleton, all of Wis.

[73] Assignee: Wisconsin Alumni Research Foundation, Madison, Wis.

[21] Appl. No.: 600,913

[22] Filed: Feb. 13, 1996

[51] Int. Cl.⁶ .................................................. A61K 31/59
[52] U.S. Cl. ................................................... 514/167
[58] Field of Search .................................... 514/167

[56] References Cited

U.S. PATENT DOCUMENTS

| | | | |
|---|---|---|---|
| 4,279,826 | 7/1981 | DeLuca et al. | 260/397.2 |
| 4,307,025 | 12/1981 | DeLuca et al. | 260/397.2 |
| 4,448,721 | 5/1984 | DeLuca et al. | 260/239.5 |
| 4,500,460 | 2/1985 | DeLuca et al. | 260/397.2 |
| 4,502,991 | 3/1985 | DeLuca et al. | 260/397.2 |
| 4,505,906 | 3/1985 | DeLuca et al. | 514/167 |
| 4,552,698 | 11/1985 | DeLuca et al. | 260/397.2 |
| 4,588,528 | 5/1986 | DeLuca et al. | 260/397.2 |
| 4,594,192 | 6/1986 | DeLuca et al. | 260/397.2 |
| 4,619,920 | 10/1986 | DeLuca et al. | 514/167 |
| 4,769,181 | 9/1988 | DeLuca et al. | 260/397.2 |
| 4,973,584 | 11/1990 | DeLuca et al. | 514/167 |
| 5,030,772 | 7/1991 | DeLuca et al. | 568/817 |
| 5,036,061 | 7/1991 | DeLuca et al. | 514/167 |
| 5,237,110 | 8/1993 | DeLuca et al. | 568/665 |
| 5,260,199 | 11/1993 | DeLuca et al. | 435/69.1 |
| 5,260,290 | 11/1993 | DeLuca et al. | 514/167 |
| 5,328,903 | 7/1994 | Ishii et al. | 514/168 |
| 5,371,249 | 12/1994 | DeLuca et al. | 552/653 |
| 5,373,004 | 12/1994 | DeLuca et al. | 514/167 |
| 5,380,720 | 1/1995 | DeLuca et al. | 514/167 |
| 5,395,830 | 3/1995 | DeLuca et al. | 514/167 |
| 5,397,775 | 3/1995 | DeLuca et al. | 514/167 |
| 5,414,098 | 5/1995 | DeLuca et al. | 552/653 |

FOREIGN PATENT DOCUMENTS

| | | |
|---|---|---|
| 0 579 915 A1 | 5/1993 | European Pat. Off. . |
| 63-104926 | 5/1988 | Japan . |
| WO 95/01960 | 1/1995 | WIPO . |

OTHER PUBLICATIONS

Muller et al., Autoimmunity, (1992) 14(1) 37–43.

D. Branisteanu, et al., "Prevention of murine experimental allergic encephalomyelitis: cooperative effects of cyclosporine and $1\alpha25-(OH)_2D_3$," *J. Neuroimmun.* 61(199):151–160, 1995.

M. Cantorna, et al., "1,25–Dihydroxyvitamin $D_3$ reversibly blocks the progression of relapsing encephalomyelits, a model of multiple sclerosis," *Proc. Natl. Acad. Sci. USA* 93:7861–7864, 1996.

J. Lemire, et al., "1,25–Dihydroxyvitamin $D_3$ Prevents the In Vivo Induction of Murine Experimental Autoimmune Encephalomyelitis," *J. Clin. Invest.* 87:1103–1107, 1991.

S. Nataf, et al., "1,25–Dihydroxyvitamin $D_3$ Exerts Regional Effects in the Central Nervous System during Experimental Allergic Encephalomyelitis," *J. Neuropath. Exp. Neurol.* 55(8):904–914, 1996.

M. Saporito, et al., "Chronic 1,25–dihydroxyvitamin $D_3$–mediated induction of nerve growth factor mRNA and protein in L929 fibroblasts and in adult rat brain," *Brain Res.* 633:189–196, 1994.

D. Tweedie, "Vitamin Treatment of Hemiplegia," *Med. J. Malaysia* 33 (2):193–194, 1978.

Ebers, George C., et al., "A Population–Based Study of Multiple Sclerosis in Twins," *N. Engl. J. Med.*, 1986; 315:1638–42.

Ebers, George C., et al., "A full genome search in multiple sclerosis," *Nature Genet.*, 1996, 13:472–76.

Haines, J.L., et al. (The Multiple Sclerosis Genetics Group), "A complete genomic screen for multiple sclerosis underscores a role for the major histocompatibility complex," *Nature Genet.*, 1996, 13:469–71.

Sawcer, Stephen, et al., "A genome screen in mutliple sclerosis reveals susceptibility loci on chromosome 6p21 and 17q22," *Nature Genet.*, 1996, 13:464–68.

Bhalla, Ashok K., et al., "1,25–Dihydroxyvitamin $D_3$ Inhibits Antigen–Induced T Cell Activation," *J. Immunol.*, 1984, 133:1748–54.

Lacey, David L., et al., "Vitamin D Affects Proliferation of a Murine T Helper Cell Clone," *J. Immunol.*, 1987, 138:1680–86.

Lemire, Jacques M., et al., "$1\alpha,25$–Dihydroxyvitamin $D_3$ Supresses Proliferation and Immunoglobulin Production by Normal Human Peripheral Blood Mononuclear Cells," *J. Clin. Invest.*, 1984, 74:657–61.

Rigby, William F.C., et al., "Inhibition of T Lymphocyte Mitogenesis by 1,25–Dihydroxyvitamin $D_3$ (Calcitriol)," *J. Clin. Invest.*, 1984, 74:1451–55.

J.–F. Bach, "Immunosuppressive therapy of autoimmune diseases," *Immun. Today* 14(6):322–326, 1993.

S. Brocke, et al., "Infection and multiple sclerosis: a possible role for superantigens?" *Trends in Microbiol.* 2(7):250–254, 1994.

S. D. Miller and W. J. Karpus, "The immunopathogenesis and regulation of T–cell–mediated demyelinating diseases," *Immun. Today* 15(8):356–361, 1994.

R. A. Rudick and D. E. Goodkin, "Measuring Impairment and Disability," *Treatment of Multiple Sclerosis: Trial Design, Results and Future Perspectives*, Springer–Verlag, London, pp. 48–53, 1992.

L. Steinman, "Escape from 'Horror Autotoxicus': Pathogenesis and Treatment of Autoimmune Disease," *Cell* 80:7–10, 1995.

*Primary Examiner*—Phyllis G. Spivack
*Attorney, Agent, or Firm*—Quarles & Brady

[57] ABSTRACT

A method of treating the multiple sclerosis symptoms of a multiple sclerosis patient is disclosed comprising administering to a multiple sclerosis patient an amount of a vitamin D compound effective to reduce symptoms and to enable an observation of a reduction in symptoms.

20 Claims, 2 Drawing Sheets

1α,25-DIHYDROXYVITAMIN $D_3$

19-NOR-1α,25-DIHYDROXYVITAMIN $D_2$

24-HOMO-22-DEHYDRO-22E-
1α,25-DIHYDROXYVITAMIN $D_3$

19-NOR-21-EPI-1α,25-DIHYDROXYVITAMIN $D_3$

MULTIPLE SCLEROSIS TREATMENT

FIELD OF THE INVENTION

The present invention relates to methods of treating multiple sclerosis. In particular, the present invention relates to the treatment of multiple sclerosis with 1,25(OH)$_2$D$_3$ and other vitamin D analogs.

BACKGROUND

Multiple Sclerosis

Multiple sclerosis (MS) is thought to result from central nervous system (CNS) demyelination, brought about by a chronic inflammatory autoimmune reaction (reviewed in Steinman, et al., *Annu. Rev. Neurosci.* 17:247, 1993; Miller, S. D. et al., *Immunol. Today* 15:356, 1994; Ffrench-Constant, C., *Lancet* 343:271–274, 1994; Brocke, S., et al., *Trends in Microbiol.* 2:250, 1994). In the animal model, experimental autoimmune encephalomyelitis (EAE), immunization of susceptible rodent strains with CNS proteins such as myelin basic protein (MBP) induces an MS-like paralytic disease. Inflamed MS and EAE lesions, but not normal white matter, have infiltrating CD4 T-cells that respond to self antigens presented by MHC class II molecules like human HLA-DR2 (MS) or murine I-A$^u$ (EAE). The infiltrating CD4 T-cells (Th1 cells) produce pro-inflammatory cytokines (interleukin (IL)-2, interferon (IFN)-$\gamma$, and tumor necrosis factor (TNF)-$\alpha$) that activate antigen-presenting cells like macrophage to produce inflammatory cytokines (IL-1$\beta$, IL-6, and IL-8) and IL-12. The IL-12 induces further IFN-$\gamma$ synthesis. In this cyclical manner, a chronic autoantigen-driven immune reaction is thought to produce a demyelinating attack on the CNS.

At least three general therapeutic approaches have been previously tried to limit the immune-mediated CNS damage in MS by targeting the effector functions of activated Th1 cells and macrophages. Antigen-non-specific immunosuppressive drugs and treatments constitute the majority of agents currently used and under study as MS therapeutics (reviewed in Noseworthy, J. H., "Immunosuppressive therapy in multiple sclerosis: pros and cons," *International MS Journal* 1:79–89, 1994). Examples are adrenocorticotrophic hormone, corticosteroid, prednisone, methylprednisone, 2-chlorodeoxyadenosine (Cladribine), mitoxantrone, sulphasalazine, methotrexate, total lymphoid irradiation, and possibly interferon-beta, although its mechanism of action remains to be defined. Some immunosuppressants have been tried without success; examples are azathioprine, cyclophosphamide, and cyclosporin. The limitations of this approach are risk of infection during non-specific immunosuppression and the toxic side effects of some of the cytotoxic drugs.

Antigen-specific immunosuppressive drugs and treatments are in development and have shown promise (Noseworthy, J. H., supra, 1994). Examples are feeding CNS antigens, such as myelin, to tolerize the encephalitogenic T-cells (Weiner, H. L., et al., *Science* 259:134, 1993), injecting pathogenic T-cells (T-cell vaccination) or synthetic T-cell receptor peptides to induce immune-mediated elimination of the pathogenic T-cells (Bourdette, D. N., et al., *J. Immunol.* 152:2510, 1994), injecting tolerogenic peptides that are related to encephalitogenic peptides of CNS antigens like myelin (Gaur, A., et al., *Science* 258:1491, 1992), and giving intravenous immunoglobulin (IVIg). The limitations of this approach are that autoantigenic epitopes are largely undefined in humans (van Noort, J. M., et al., *Nature* 375:798, 1995), and these epitopes and TCR sequences may differ between MS patients, and within a single MS patient, as the autoimmune reaction spreads to additional epitopes within one protein and to additional proteins (Lehmann, et al., *Nature* 358:155, 1992).

Cytokine-specific therapies are in development (Noseworthy, J. H., supra, 1994). Examples are neutralizing antibodies against tumor necrosis factor (TNF), soluble TNF-receptors, soluble interleukin-1 antagonists, and others. The limitations of these approaches are the problem of delivering the neutralizing agent in sufficient quantity to the CNS tissue site where it is required, and the immunological side effects of long-term cytokine neutralizing activity.

A preliminary insight into the treatment proposed here was provided by the experiments of Lemire, et al., (Lemire, J. M., et al., *J. Clin. Invest.* 87:1103, 1991), who decreased the disease incidence and severity but did not prevent EAE by feeding mice a low calcium diet and injecting 1,25(OH)$_2$D$_3$ before and after disease induction. In these experiments, it is unclear which was the effective manipulation, the low calcium diet or the 1,25(OH)$_2$D$_3$ treatment.

1,25(OH)$_2$D$_3$ and Analogs

The 1$\alpha$-hydroxylated metabolites of vitamin D—most importantly 1$\alpha$,25-dihydroxyvitamin D$_3$ and 1$\alpha$,25-dihydroxyvitamin D$_2$—are know as highly potent regulators of calcium homeostasis in animals and humans. More recently, their activity in cellular differentiation has also been established. As a consequence, many structural analogs of these metabolites, such as compounds with different side-chain structures, different hydroxylation patterns, or different stereochemistry, have been prepared and tested. Important examples of such analogs are 1$\alpha$,25-dihydroxyvitamin D$_3$, 1$\alpha$,25-dihydroxyvitamin D$_2$, various side-chain fluorinated derivatives of 1$\alpha$,25-dihydroxyvitamin D$_3$, and side-chain homologated analogs. Several of these known compounds exhibit highly potent activity in vivo or in vitro, and possess advantageous activity profiles and thus are in use, or have been proposed for use, in the treatment of a variety of diseases such as renal osteodystrophy, vitamin D-resistant rickets, osteoporosis, psoriasis, and certain malignancies.

SUMMARY OF THE INVENTION

The present invention is a method of treating multiple sclerosis patients by administering an amount of a vitamin D compound, preferably 1,25(OH)$_2$D$_3$ or analogs thereof, effective to diminish the multiple sclerosis symptoms. The method comprises selecting a multiple sclerosis patient and administering a sufficient amount of the vitamin D analog to the patient such that the multiple sclerosis symptoms are abated.

In a particularly advantageous form of the reaction, the administered compound is either 1$\alpha$,25-dihydroxyvitamin D$_3$ (1,25-(OH)$_2$D$_3$), 19-nor-1,25-dihydroxyvitamin D$_2$ (19-nor-1,25-(OH)$_2$D$_2$), 24-homo-22-dehydro-22E-1$\alpha$,25-dihydroxyvitamin D$_3$ (24-homo-22-dehydro-22E-1,25-(OH$_2$)D$_3$, 1,25-dihydroxy-24(E)-dehydro-24-homo-vitamin D$_3$ (1,25-(OH)2-24-homoD$_3$), or 19-nor-1,25-dihydroxy-21-epi-vitamin D$_3$ (19-nor-1,25-(OH)$_2$-21-epi-D$_3$).

A preferred dose of vitamin D compound for the present invention is the maximum that a patient can tolerate and not develop serious hypercalcemia. If the vitamin D compound is not a 1$\alpha$-hydroxy compound, a particularly advantageous daily dose of vitamin D compound is between 5.0 and 50 µg per day per 160 pound patient. If the vitamin D compound is a 1$\alpha$-hydroxy compound, the preferred dose is between 0.5 and 10 µg per day per 160 pound patient. If the patient has normal calcium intakes, doses of $1,25(OH_2)D_3$ over 0.5–0.75 µg per day per 160 pound patient are not preferred. If the patient is on a low calcium diet and/or takes the dose late at night, higher doses of $1,25(OH_2)D_3$ would be possible and would be preferred. In this embodiment of the invention, the amount of $1,25(OH_2)D_3$ administered could be as high as 5 µg per day per 160 pound patient. A preferred dose would be 3 µg per day per 160 pound patient.

It is an advantage of the present invention that the method diminishes the symptoms of multiple sclerosis.

It is another advantage of the present invention that the method suppresses autoreactive effector cells.

It is another advantage of the present invention that the method reduces TNF-α and INF-α gene activation.

It is another advantage of the present invention that the method increases transforming growth factor TGF-β gene expression.

It is another advantage that the method can be used to prevent the disease in patients genetically predisposed to multiple sclerosis.

Other advantages and features of the present invention will become apparent after examination of the specification, claims and drawings.

DESCRIPTION OF THE INVENTION

1. In General

Figure 1:
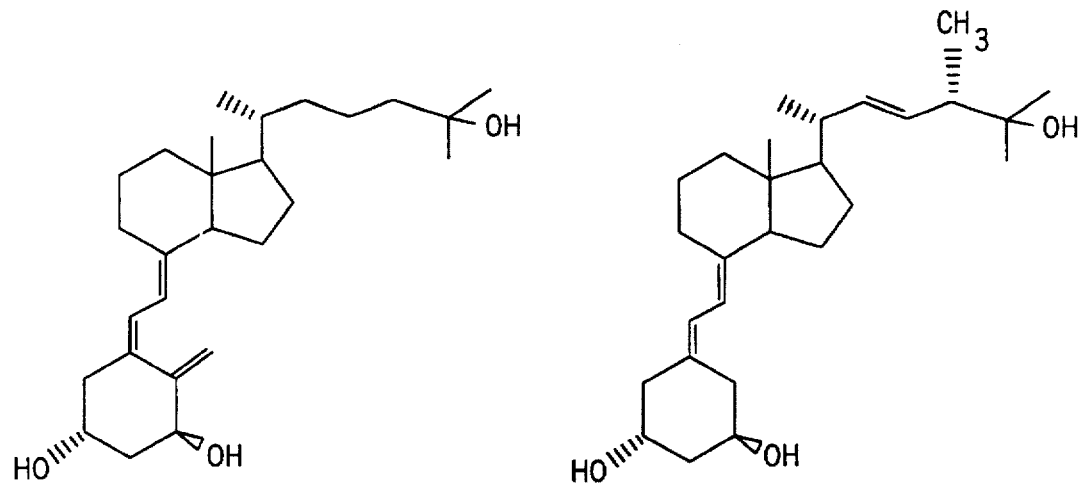
FIG. 1 is a diagram of suitable vitamin D compounds for the present invention.
Figure 1:
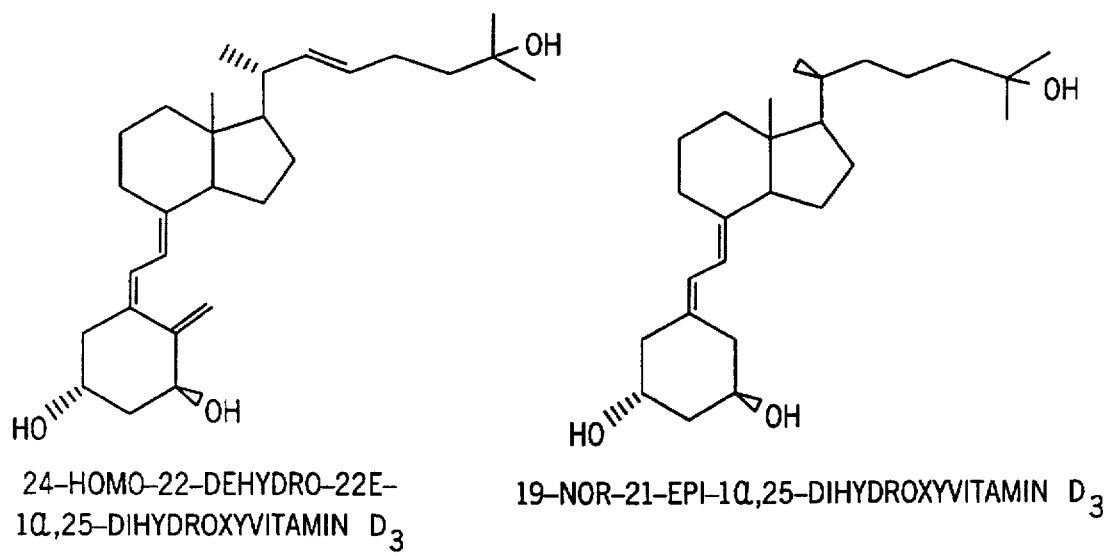

We envision a fundamentally different therapeutic approach to multiple sclerosis using vitamin D compounds.

Neither our previous experiments (Cantorna, M. T., et al., *Eur. J. Immunol.* 25:1673, 1995; Carman, J. A., et al., *J. Exp. Med.* 175:111, 1992; Cantorna, M. T., et al., *J. Immunol.* 152:1515, 1994; Chun, T., et al., *J. Nutr.* 122:1062, 1992), nor those of Lemire and colleagues (Lemire, J. M., et al., *J. Cellular Biochem.* 49:26, 1992) address the critical issue of whether vitamin D can act at the priming stage to regulate the differentiation of the Th0 precursors into Th1 or Th2 cells, in addition to acting at the effector stage to regulate cytokine gene expression. This issue is critical to MS therapy because as the disease progresses, the autoimmune reaction spreads to additional MPB epitopes and to additional proteins, indicating an ongoing process of encephalytic Th1 cell priming (Lehmann, P. V., et al., supra, 1992). We hypothesize that vitamin D treatment could limit an inflammatory cycle by virtue of its ability to regulate the differentiation of Th0 precursors, as well as its ability to regulate Th1 cell effector function.

Our experiments below are conducted with an accepted experimental model for multiple sclerosis, B10.PL mice, known to have histopathological and clinical similarities to the relapsing-remitting form of the human disease (Miller and Karpus, *Immun. Today* 15[8]:356, 1994). These mice exhibit experimental autoimmune encephalomyelitis (EAE) in response to injection with the myelin basic protein (MBP). EAE is an experimentally induced, $CD4^+$ T-cell-mediated autoimmune disease that is directed against protein components of CNS myelin (Miller, et al., supra, 1994). The EAE is characterized by transient ascending paralysis of the affected mouse's limbs.

2. Treatment of MS Patients a. Reduction of multiple sclerosis symptoms.

The present invention is suitable for the reduction of multiple sclerosis symptoms. By "multiple sclerosis symptoms," we mean the commonly observed symptoms of multiple sclerosis, such as those described in *Treatment of Multiple Sclerosis: Trial Design, Results, and Future Perspectives*, e.d. Rudick and D. Goodkin, Springer-Verlag, New York, 1992, particularly those symptoms described on pages 48–52. (This document is incorporated by reference as if fully set forth herein.)

These multiple sclerosis symptoms include perturbations of pyramidal functions, for example the development of paraparesis, hemiparesis, monoparesis and quadriparesis and the development of monoplegia, paraplegia, quadriplegia, and hemiplegia. The symptoms of multiple sclerosis also include perturbations in cerebellar functions. These perturbations include the development of ataxia, including truncal and limb ataxia. When we refer to "paralytic symptoms of multiple sclerosis" we are referring to these perturbations in pyramidal and cerebellar functions.

The symptoms of multiple sclerosis also include changes in brain stem functions including development of nystagmus and extraocular weakness along with dysarthria. Further symptoms include loss of sensory function including decrease in touch or position sense and loss of sensation in limbs. Perturbations in bowel and bladder function, including hesitancy, urgency, retention of bowel or bladder or incontinence, can also occur. Visual functions, such as the development of scotoma, are also affected by multiple sclerosis. Cerebral function degeneration, including a decrease in mentation and the development of dementia, is also a symptom.

The present invention is envisioned as retarding the onset and reducing the severity of any or all symptoms of multiple sclerosis, most particularly the paralytic symptoms. The severity of the disease, and its subsequent relief, can be measured by a scale such as the Expanded Disability Status Scale (EDSS) described in Rudick and Goodkin, supra, or a decrease in the frequency of relapses, or an increase in the time to sustained progression, or improvement in the magnetic resonance imaging (MRI) behavior in frequent, serial MRI studies.

b. Treatment plan

We propose a dose or "effective amount" of vitamin D compound of between 0.5–50 µg per day for a 160 pound patient. If the compound is a 1α-hydroxy compound, the preferred dose is between 0.5–10 µg per day for a 160 pound patient. Preferably, the dose is between 0.75–10 µg per day. Most preferably, the dose is between 3–10 µg a day. In general, the dose should be the highest amount of the vitamin D compound that the patient can tolerate. The dose is preferably divided between two and three treatments per day.

The accepted safe dose of $1,25(OH_2)D_3$ and 19-nor-21-epi-$1,25(OH_2)D_3$ in patients having normal calcium intakes in the United States is between 0.5 and 15 µg per day for $1,25-(OH)_2D_3$ and is 10–20 µg/day for 19-nor-$1,25-(OH)_2D_2$. Therefore, the preferable dose for patients with normal calcium intakes is between 0.5 and 0.75 µg per day for a 160 pound patient depending on the compound administered.

If patients are shifted to low calcium diet and given $1,25(OH)_2D_3$ (calcitriol) and/or given the vitamin D compound at night, more 1,25(OH)₂D₃ (up to 3 μg per day) can be tolerated. Therefore, one advantageous embodiment of the present invention would be to treat the patient with 1,25(OH)₂D₃ in as high a dose as the patient can tolerate without getting serious hypercalcemia. This additional level of calcitriol treatment would enable doses as high as 3 μg per day and possibly as high as 10 μg per day. Therefore, the preferable dose for patients with a manipulated calcium content is the above-stated dose of between 0.75-10 μg per day and, most preferably, a dose of between 3-10 μg per day.

The safe dose range for 19-nor-1,25(OH₂)D₂ and 24-homo-22-dehydro-22E-1α,25(OH₂)D₃ is 10-20 μg per day per 160 pound patient.

This vitamin D dose may be taken orally in a capsule, pill, or lozenge, or via injection, skin patch, or suppository. The oral administration is the preferred method.

To evaluate whether a patient is benefitting from the vitamin D treatment, one would examine the patient's symptoms in a quantitative way, such as by the EDSS mentioned above (Rudick and Goodkin, supra), or decrease in the frequency of relapses, or increase in the time to sustained progression, or improvement in the magnetic resonance imaging (MRI) behavior in frequent, serial MRI studies and compare the patient's status measurement before and after treatment. In a successful treatment, the patient status will have improved (i.e., the EDSS measurement number or frequency of relapses will have decreased, or the time to sustained progression will have increased, or the MRI scans will show less pathology).

Preferably, treatment should continue as long as multiple sclerosis symptoms are suspected or observed.

3. Vitamin D Analogs

Preferred compounds for the practice of the present invention include vitamin D compounds that are approximately equal to 1,25(OH₂)D₃ in lessening a multiple sclerosis patient's symptoms, particularly paralytic symptoms, while producing fewer side effects. Preferably, 1α-hydroxy vitamin D compounds will be chosen. Applicants have tested the compounds shown in FIG. 1 and demonstrated success with these compounds. Preferred compounds for the practice of the present invention include 1,25-dihydroxyvitamin D₃ (1,25-(OH)₂D₃), 1α-hydroxyvitamin D₃ (1α-OH-D₃), 1,25-dihydroxyvitamin D₂ (1,25-(OH)₂D₂), 1α-hydroxyvitamin D₂ (1α-OH-D₂), 26,27-hexafluoro-1,25-dihydroxyvitamin D₂ (F₆-1,25-(OH)₂D₃), 19-nor-1,25-dihydroxyvitamin D₂ (19-nor-1,25-(OH)₂D₂), 1,25-dihydroxy-24(E)-dehydro-24-homo-vitamin D₃ (1,25-(OH)₂-24-homoD₃), and 19-nor-1,25-dihydroxy-21-epi-vitamin D₃ (19-nor-1,25-(OH)₂-21-epi-D₃). 1α,25 dihydroxyvitamin D₃ triacetate and 25-acetyl-1α,25 dihydroxyvitamin D₃ are also preferred compounds.

In order to evaluate whether a candidate vitamin D analog is suitable for the present invention, one would test the analog side-by-side with 1,25-(OH)₂D₃ and determine the effective dose of the compound in alleviating multiple sclerosis symptoms as compared to the dose that produces hypercalcemia. A successful compound would have a high ratio of activity against multiple sclerosis to its ability to produce hypercalcemia. A ratio superior to or equal to 1,25-(OH)₂D₃ is considered highly successful.

Compounds believed to be effective in the present invention include:

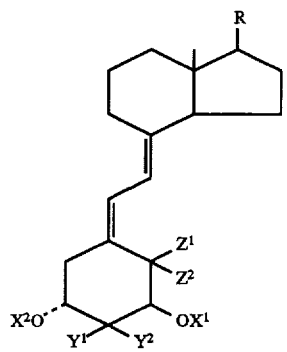

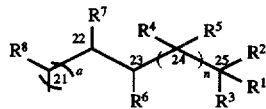

wherein X¹ and X² are each selected from the group consisting of hydrogen and acyl;

wherein Y¹ and Y² can be H, or one can be O-aryl or O-alkyl while the other is hydrogen and can have a β or α configuration; Z¹=Z²=H or Z¹ and Z² together are CH₂; and wherein R is an alkyl, hydroxyalkyl or fluoroalkyl group, or R may represent the following side chain:

wherein a may have an S or R configuration and wherein R¹ represents hydrogen, hydroxy or O-acyl, R² and R³ are each selected from the group consisting of alkyl, hydroxyalkyl and fluoroalkyl, or, when taken together represent the group—(CH₂)ₘ—where m is an integer having a value of from 2 to 5, R⁴ is selected from the group consisting of hydrogen, hydroxy, fluorine, O-acyl, alkyl, hydroxyalkyl and fluoroalkyl, R⁵ is selected from the group consisting of hydrogen, hydroxy, fluorine, alkyl, hydroxyalkyl and fluoroalkyl, or, R⁴ and R⁵ taken together represent double-bonded oxygen, R⁶ and R⁷ taken together form a carbon—carbon double bond and R⁸ may be H or CH₃, and wherein n is an integer having a value of from 1 to 5, and wherein the carbon at any one of positions 20, 22, or 23 in the side chain may be replaced by an O, S, or N atom.

In this specification and the claims, the term "alkyl" signifies an alkyl radical of 1 to 5 carbons in all isomeric forms, such as methyl, ethyl, propyl, isopropyl, butyl, isobutyl, pentyl, etc., and the terms "hydroxyalkyl" and "fluoroalkyl" refer to such an alkyl radical substituted by one or more hydroxy or fluoro groups respectively. The term "acyl" means an aliphatic acyl group of 1 to 5 carbons, such as formyl, acetyl, propionyl, etc. or an aromatic acyl group such as benzoyl, nitrobenzoyl or halobenzoyl. The term "aryl" signifies a phenyl-, or an alkyl-, nitro- or halo-substituted phenyl group.

4. Mechanism of Action

Based on our data presented below in the Examples, we can make the following observations: Vitamin D decreases the Th1 cell frequency during priming (as evidenced by IFN-γ and TNF-α measurements in Table 4). Vitamin D increases the Th2 cell frequency during priming (as evidenced by IL-4 measurements in Table 4). Vitamin D increases TGF-β synthesis (as evidenced by TGF-β measurements in Tables 5 and 6). Vitamin D decreases encephalitogenic cell effector function (as evidenced by FIGS. 2 and 3).

Therefore, in another embodiment, the present invention is a method of suppressing Th1 cell frequency. This suppression may be measured as described below in the Examples.

In human HIV patients, Th1 cell frequency has been examined by lymph node biopsy and cytokine transcript analysis (Grazios, C., et al., *Science* 265:248, 1994).

EXAMPLES

1. In General

The Examples below are designed to demonstrate several embodiments of the present invention. Example 3(A) demonstrates that $1,25(OH)_2D_3$ treatment after disease induction prevents the progression of EAE in B10.PL mice. Example 3(B) demonstrates that removal of $1,25(OH)_2D_3$ results in the resumption of progressive EAE in B10.PL mice. Example 3(C) demonstrates that unlike any other study, $1,25(OH)_2D_3$ and analogs thereof completely prevent EAE, or delay the onset and reduce the severity of EAE when administered before disease induction. Example 3(D) demonstrates that vitamin D deficiency accelerates the day of EAE onset, and Example 3(E) demonstrates that a low calcium diet reduces the proportion of mice that develop EAE. Example 3(F) demonstrates that vitamin D treatment in vivo reduces MBP reactive Th1 cell development and cytokine gene activation and increases MBP reactive Th2 cell development and cytokine gene activation. Examples 3(G) and 3(H) demonstrate that $1,25-(OH)_2D_3$ treatment in vivo and in vitro increases TGF-$\beta$ gene expression.

2. Materials and Methods

Animals. B10.PL mouse breading pairs were obtained from Jackson Laboratories (Bar Harbor, Me.). The experiments below used weight-matched male and female mice, 5 to 8 weeks of age, which were either raised on a diet devoid of vitamin D (vitamin D deficient) or raised on a diet with normal levels of vitamin D (vitamin D sufficient). Experimental diets (Smith, S. M., et al., *J. Nutr.* 117:857, 1987 as modified by Yang, et al., *Arch. Biochem. Biophys.* 303:98–106, 1993) which contained no additional vitamin D were made and replaced every 2–3 days for the duration of the experiment.

For experiments which used a low calcium diet; the same experimental diet, containing no additional vitamin D, was made except the dietary source of calcium (calcium carbonate) was not added (0.02% $Ca^{2+}$ diet).

Mice were split into groups of 8–12 mice; one group was fed the experimental diet alone, other groups were fed the experimental diet plus various concentrations of 1,25-dihydroxyvitamin $D_3$ ($1,25-(OH)_2D_3$), or 19-nor-1,25-dihydroxyvitamin $D_2$ (19-nor-$1,25-(OH)_2D_2$), or 1,25-dihydroxy-24(E)-dehydro-24-homo-vitamin $D_3$ ($1,25-(OH)_2$-24-homoD$_3$), or 19-nor-1,25-dihydroxy-21-epi-vitamin $D_3$ (19-nor-$1,25-(OH)_2$-21-epi-$D_3$).

At the end of the experiments mice were sacrificed, weighed, and bled for serum calcium analysis.

Reagents. Myelin basic protein (MBP) was isolated from guinea pig spinal cords following the procedure of Deibler, et al. (Deibler, G. E., et al., *Prep. Biochem.* 2:139, 1972). MBP was lyophilized and stored at $-20°$ C. For immunizations MBP was dissolved in 0.1M acetic acid at a concentration of 8 mg/ml. Pertussis toxin was purchased from LIST Biological Laboratories (Campbell, Calif.) and resuspended in sterile saline. MBP was emulsified in an equal volume of complete Freund's adjuvant (CFA) containing Mycobacterium tuberculosis $H_{37}$ Ra (4 mg/ml).

EAE induction. Ether-anesthetized mice were immunized s.c. with 0.1 ml of MBP (400 µg/mouse) emulsified in CFA. On the day of immunization and two days later mice were additionally injected i.p. with 200 ng of pertussis toxin. This immunization protocol resulted in the induction of experimental autoimmune encephylmyelitis (EAE) or the equivalent of human multiple sclerosis.

Disease severity. Mice were scored daily using a standard scoring system for EAE in mice (Clayton, J. P., et al., *J. Exp. Med.* 169:1681, 1989). The scoring was as follows; 0-no paralysis, 1-tail limp/slow/dull eyes, 2-partial hind paralysis or limb weakness, 3-difficulty turning over, severe limb weakness or mild paralysis, 4-severe to total paralysis, 5-moribund/dead.

Vitamin D treatment. In Examples 3(A) and 3(B), the treatment was given after disease induction. Two groups of 12 age and sex matched B10.PL mice were immunized with MBP in CFA as described above. When individual mice showed EAE symptoms of 1 or greater they were given an intraperitoneal injection containing 300 ng of $1,25(OH)_2D_3$ dissolved in ethanol or mock injected with an equivalent amount of ethanol. At the time of $1,25(OH)_2D_3$ treatment, the diet was also changed to the experimental diet that provided no additional vitamin D or to a diet containing 20 ng/day per mouse of $1,25(OH)_2D_3$. All the mice showed symptoms of EAE by day 10 post-immunization. On day 18 post-immunization, $1,25(OH)_2D_3$ was removed from the diet of half the mice being treated with $1,25(OH)_2D_3$.

This protocol created three groups of mice. The first group of mice were mock-treated and maintained on a diet devoid of vitamin D. The second group of mice were treated with $1,25(OH)_2D_3$ for 8–12 days and then placed on a diet devoid of vitamin D. The third group of mice were treated with $1,25(OH)_2D_3$ and maintained on a diet containing 20 ng/day per mouse of $1,25(OH)_2D_3$ for the remainder of the study.

In Example 3(C), the vitamin D treatment was given one day before disease induction. The disease was induced and analyzed in the treated and control groups as described above.

3. Results

A. $1,25(OH_2D_3$ Prevents the Progression of EAE in B10.PL Mice.

When individual mice showed EAE symptoms of 1 or greater they were given an intraperitoneal injection containing 300 ng of $1,25(OH)_2D_3$ dissolved in ethanol (●) or mock injected with an equivalent amount of ethanol (○).

Figure 2:
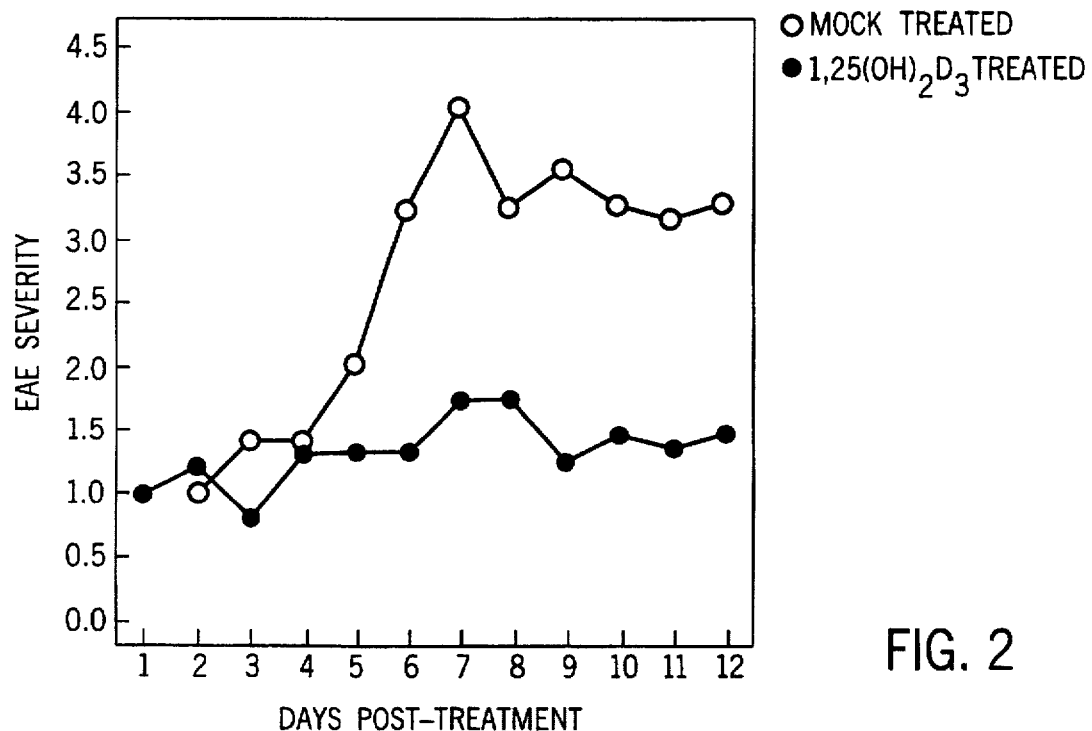
FIG. 2 is a graph of EAE severity as a function of days post-treatment with either $1,25(OH)_2D_3$ or mock treatment.

At the time of treatment the diet was also changed to the experimental diet containing no additional vitamin D or to a diet that delivered 20 ng/day per mouse of $1,25(OH)_2D_3$. FIG. 2 diagrams the results of this experiment and demonstrates that $1,25(OH)_2D_3$ prevents the progression of EAE in B10.PL mice. Note that the mice that had been treated with $1,25(OH)_2D_3$ exhibited less EAE severity than the mock-treated animals.

B. Removal of $1,25(OH)_2D_3$ Results in Increased EAE Symptoms in B10.PL Mice.

Figure 3:
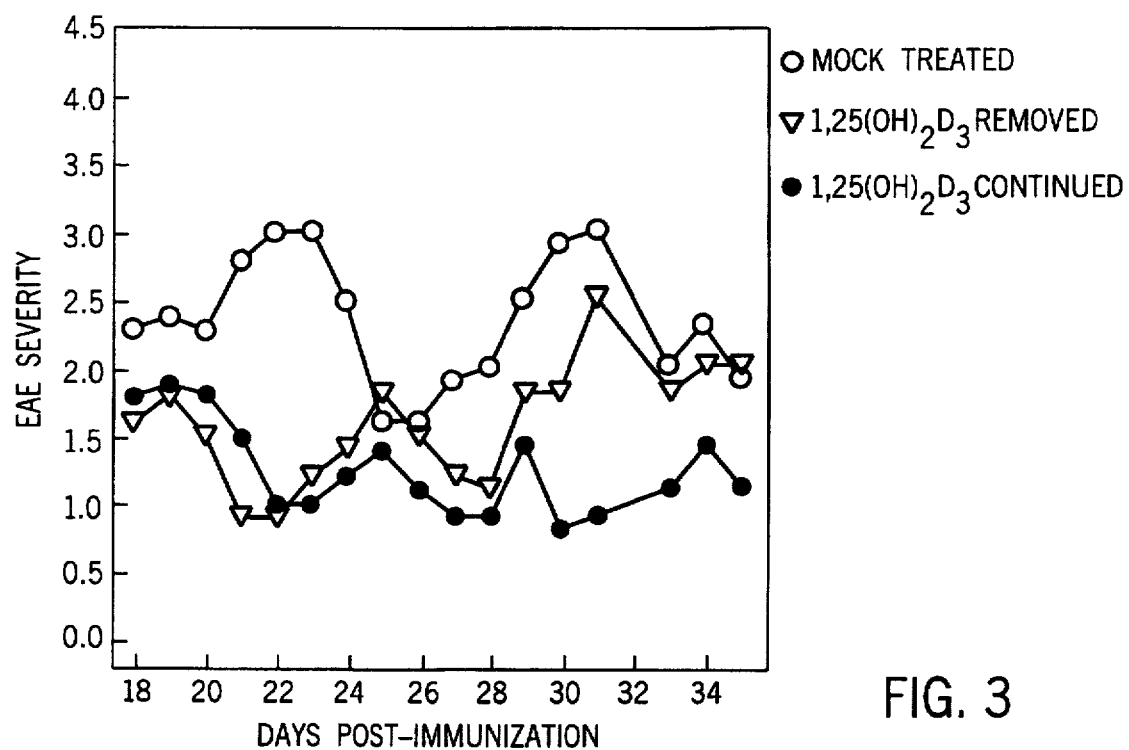
FIG. 3 is a graph of EAE severity as a function of days post-immunization with either $1,25(OH)_2D_3$ treatment continued, $1,25(OH)_2D_3$ treatment removed, or mock-treatment.

The mice from FIG. 2 were split into three new groups. The first group of mice were mock-treated and maintained on a diet devoid of vitamin D (○). The second group of mice were treated with $1,25(OH)_2D_3$ for 8–12 days and then placed on a diet devoid of vitamin D (▽). The third group of mice were treated with $1,25(OH)_2D_3$ and maintained on a diet providing 20 ng/day per mouse for the remainder of the study (●). Removal of $1,25(OH)_2D_3$ from the diet of previously $1,25(OH)_2D_3$ treated mice resulted in increased EAE symptoms compared to controls which continued to be fed $1,25(OH)_2D_3$. FIG. 3 diagrams the results of this experiment and demonstrates that removal of 1,25(OH)$_2$D$_3$ results in increased EAE symptoms in B10.PL mice.

C. 1,25-(OH)$_2$D$_3$ and analogs thereof either delay or completely prevent EAE onset and reduce the severity of EAE.

We examined the effect of 1,25(OH)$_2$D$_3$ and analogs thereof on the onset and severity of EAE by transferring B10.PL mice with normal vitamin D levels (vitamin D sufficient) to a diet containing no additional vitamin D or the amounts of 1,25(OH)$_2$D$_3$ or analogs shown in Table 1. The diet was changed on the day before the induction of experimental autoimmune encephalomyelitis (EAE).

The mice were immunized with MBP as above and analyzed for disease onset, severity, weight, and serum Ca. The 1,25-dihydroxy vitamin D$_3$ and analogs thereof completely prevented EAE, unlike any other study, or delayed the onset and reduced the severity of EAE. Table 1 tabulates the results of this experiment.

Table 1(C) demonstrates that mice treated with 1,25(OH)$_2$-24-homo-22-dehydro-22E-D$_3$ at 200 ng/day never developed EAE symptoms.

Table 1(D) shows that mice treated with 19-nor 1,25(OH)$_2$-21-epi-D$_3$ never developed EAE symptoms.

D. Vitamin D deficiency accelerates the day of EAE onset.

Vitamin D-deficient B10.PL mice were produced by placing a pregnant female on a D-deficient diet, and then maintaining her pups on that diet. EAE was induced at 5 weeks of age in vitamin D-deficient or vitamin D-sufficient B10.PL mice. The mice were analyzed for disease onset, severity, weight, and serum Ca. Vitamin D deficiency accelerated the day of EAE onset compared to vitamin D-sufficient controls. The results of this experiment are tabulated below in Table 2.

TABLE 1

| Diet | Day of onset | Peak severity | Incidence (#paralyzed/#tested) | Terminal weight (g) | Terminal serum Ca (mg %) |
| --- | --- | --- | --- | --- | --- |
| A | | | | | |
| no added D | 18 ± 8 | 4.0 | 11/11 | 20.4 ± 3.1 | 8.1 ± 0.6 |
| 1,25-(OH)$_2$D$_3$ 20 ng/day | none | 0 | 0/9 | 19.1 ± 4.8 | 10.9 ± 0.8 |
| 1,25-(OH)$_2$D$_3$ 100 ng/day | none | 0 | 0/9 | 14.3 ± 1.7 | 11.6 ± 0.5 |
| B | | | | | |
| no added D | 20 ± 10 | 3.5 | 11/11 | 22.2 ± 3.5 | 8.3 ± 0.5 |
| 19-nor 1,25(OH)$_2$-D$_2$ 100 ng/day | 32 ± 4 | 2.0 | 8/11 | 20.0 ± 3.6 | 10.2 ± 0.7 |
| C | | | | | |
| no added D | 26 ± 9 | 3.5 | 11/11 | 22.7 ± 3.4 | 8.5 ± 0.2 |
| 19-nor 1,25(OH)$_2$D$_2$ 200 ng/day | none | 0 | 0/9 | 15.7 ± 2.0 | 14.4 ± 1.7 |
| 19-nor 1,25(OH)$_2$D$_2$ 400 ng/day | none | 0 | 0/11 | 13.5 ± 1.0 | 14.1 ± 2.5 |
| 1,25-(OH)$_2$-24-homo-22-dehydro-22E-D$_3$ 180 ng/day | 31 ± 11 | 1.0 | 4/11 | 21.2 ± 5.7 | 11.1 ± 0.7 |
| 1,25-(OH)$_2$-24-homo-22-dehydro-22E-D$_3$ 360 ng/day | none | 0 | 0/11 | 16.8 ± 4.2 | 12.8 ± 1.1 |
| D | | | | | |
| no added D 20 ng/day | 16 ± 7 | 3.5 | 8/8 | 21.6 ± 3.3 | 10.1 ± 0.6 |
| 19-nor-1,25(OH)$_2$-21-epi-D$_3$ | none | 0 | 0/9 | 14.3 ± 1.9 | 17.3 ± 2.9 |

EAE storing system: 0 = normal, 1 = limp tail, 2 = paraparesis with a clumsy gait, 3 = hind limb paralysis, 4 = hind and fore limb paralysis, 5 = death.

Table 1(A) demonstrates that mice given either 20 ng/day or 100 ng/day of 1,25(OH)$_2$D$_3$ did not develop EAE symptoms, in comparison to control mice which developed EAE symptoms at approximately 18 days.

Table 1(B) demonstrates that mice treated with 19-nor 1,25(OH)$_2$-D$_2$ developed EAE later and with less severity than control mice.

Table 1(C) demonstrates that mice treated with 19-nor 1,25(OH)$_2$-D$_2$ at 200 ng/day and 400 ng/day never developed EAE. Nice treated with 1,25(OH)$_2$-24-homo-22-dehydro-22E-D$_3$ developed EAE with a peak severity of only 1 at 31 days as compared to a peak severity of 3.5 at 27 days for the control mice.

TABLE 2

| Mice | Day of onset | Peak severity | Incidence | Terminal weight (g) | Serum Ca (mg %) |
| --- | --- | --- | --- | --- | --- |
| D-sufficient | 20 ± 10 | 3.5 | 11/11 | 22.2 ± 3.5 | 8.3 ± 0.5 |
| D-deficient | 12 ± 4 | 3.0 | 8/8 | 17.3 ± 4.2 | 4.7 ± 0.1 |

EAE scoring system: 0 = normal, 1 = limp tail, 2 = paraparesis with a clumsy gait, 3 = hind limb paralysis, 4 = hind and fore limb paralysis, 5 = death.

Table 2 demonstrates that vitamin D deficient mice develop onset of EAE symptoms approximately 8 days earlier than vitamin D sufficient mice.

E. A low calcium diet reduces the proportion of mice which develop EAE.

Mice with normal vitamin D levels (vitamin D sufficient) were maintained on a normal calcium diet (1.2%) or transferred to a low calcium diet (0.02%) on the day before the induction of experimental autoimmune encephalomyelitis (EAE). The mice were compared for the day of disease onset. The results of this experiment are tabulated below in Table 3. As Table 3 demonstrates, a change in the amount of calcium available in the diet reduced the proportion of mice which developed EAE.

TABLE 3

| Treatment in vivo | Incidence |
|---|---|
| normal calcium diet | 41/41 |
| low calcium diet | 6/13 |

Our interpretation of this result is that low serum calcium stimulates parathyroid secretion which in turn increases endogenous $1,25$-$(OH)_2D_3$ levels. The actual protection is caused by the increased $1,25$-$(OH)_2D_3$ levels.

Thus, in normally fed mice, a low calcium diet is beneficial and could account entirely for the results of Lemire et al, supra.

F. Vitamin D treatment in vivo reduces MBP-reactive Th1 cell development and/or cytokine gene activation.

Mice were given injections of $1,25$-$(OH)_2D_3$ in EtOH or EtOH every other day, from the day of priming with myelin basic protein in Freund's complete adjuvant to the day of cell harvest ten days later. Lymph node cells were collected and restimulated five days in vitro with MBP prior to cytokine transcript analysis by quantitative competitive-PCR. The results are tabulated below in Table 4.

The data in Table 4 suggests that $1,25$-$(OH)_2D_3$ suppresses EAE by suppressing the generation of autoreactive Th1 cells which make interleukin (IL-)-2, interferon-gamma (IFN-γ), and tumor necrosis factor-alpha (TNF-α). IFN-γ and TNF-α are inflammatory mediators which have been shown by others to be pivotal for the development of EAE. The data also suggests that $1,25$-$(OH)_2D_3$ is a positive regulator of MBP reactive cells which make interleukin (IL-)-4. IL-4 is a negative regulator of Th1 cells which make IL-2, IFN-γ and TNF-α.

TABLE 4

| Treatment in vivo | Cytokine transcripts per 10,000 G3PDH transcripts | | | |
|---|---|---|---|---|
| | IL-2 | IFN-γ | TNF-α | IL-4 |
| EtOH only | 1.7 | 0.34 | 509 | 0.0 |
| 1,25-(OH)₂D₃ in EtOH | 0.7 | 0.22 | 331 | 3.5 |

G. Vitamin D in vivo increases TGF-β gene expression.

Mice with normal vitamin D levels (vitamin D-sufficient) were transferred to a diet providing no additional vitamin D or 20 ng/day/mouse of $1,25$-$(OH)_2D_3$. The diet was changed on the day before the induction of EAE. Lymph node cells were collected at 7 and 14 days post-immunization. RNA was collected and cytokine transcripts were quantitated by competitive-PCR. Cytokine transcripts were measured in the absence of in vitro restimulation (compared to Table 4). Table 5 is a tabulation of these data. The data in Table 5 suggests that $1,25$-$(OH)_2D_3$ increases TGF-β synthesis on day 14 post-immunization. (TGF-β is a negative regulator of Th1 cells and EAE.)

TABLE 5

| Treatment in vivo | Days post-immunization | Cytokine transcripts per 1000 G3PDH transcripts | | | | |
|---|---|---|---|---|---|---|
| | | TGF-β | IL-2 | IFN-γ | TNF-α | IL-4 |
| EtOH only | 7 | 7.6 | 20.6 | 15.4 | 0.5 | 0.2 |
| | 14 | 3.8 | 65.9 | 19.2 | 0.9 | 0.0 |
| 1,25-(OH)₂D₃ in EtOH | 7 | 0.1 | 5.2 | 0.0 | 0.0 | 0.2 |
| | 14 | 60.9 | 131.9 | 0.2 | 0.9 | 0.0 |

H. Vitamin D in vitro increases TGF-β gene expression.

Plastic adherent peritoneal exudate cells (primarily macrophage) from vitamin D-deficient mice were treated with lipopolysaccharide in vitro in the presence or absence of $1,25(OH)_2D_3$. The data is tabulated below in Table 6. Vitamin D addition in vitro induced a 3-fold increase in the number of TGF-β transcripts. These data support the information in Table 5.

TABLE 6

| treatment in vitro | TGF-β transcripts per 1000 G3PDH transcripts |
|---|---|
| EtOH only | 24.6 |
| 1,25-(OH)₂D₃ in EtOH | 98.6 |

We claim:

1. A method of treating the multiple sclerosis symptoms of a multiple sclerosis patient comprising administrating to the patient an amount of a vitamin D compound effective to reduce symptoms and to enable an observation of a reduction in symptoms.

2. The method of claim 1 wherein the symptoms are paralytic symptoms.

3. The method of claim 1 wherein the vitamin D compounds are 1α-hydroxy compounds.

4. The method of claim 3 wherein the compound is $1,25(OH)_2D_3$.

5. The method of claim 1 wherein the amount of vitamin D analog administered is between 0.5 and 50 µg per day per 160 pound patient.

6. The method of claim 3 wherein the amount of vitamin D analog administered is between 0.5 and 0.75 µg per day per 160 pound patient.

7. The method of claim 3 wherein the amount of vitamin D analog administered is between 3.0 and 10 µg per day per 160 pound patient.

8. A method of treating the multiple sclerosis symptoms of a multiple sclerosis patient comprising the steps of administering to the patient an effective amount of the following compound:

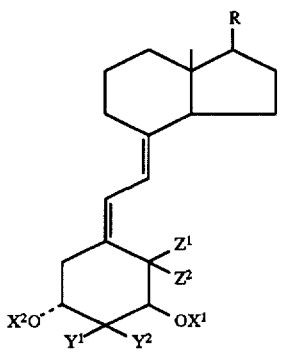

wherein $X^1$ and $X^2$ are each selected from the group consisting of hydrogen and acyl;

wherein $Y^1$ and $Y^2$ can be H, or one can be O-aryl or O-alkyl and can have a β or α configuration; $Z^1=Z^2=H$ or $Z^1$ and $Z^2$ together are $CH_2$; and wherein R is an alkyl, hydroxyalkyl or fluoroalkyl group, or R may represent the following side chain:

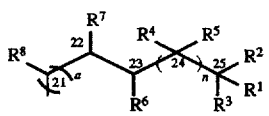

wherein (a) may have an S or R configuration, $R^1$ represents hydrogen, hydroxy or O-acyl, $R^2$ and $R^3$ are each selected from the group consisting of alkyl, hydroxyalkyl and fluoroalkyl, or, when taken together represent the group—$(CH_2)_m$—where m is an integer having a value of from 2 to 5, $R^4$ is selected from the group consisting of hydrogen, hydroxy, fluorine, O-acyl, alkyl, hydroxyalkyl and fluoroalkyl, $R^5$ is selected from the group consisting of hydrogen, hydroxy, fluorine, alkyl, hydroxyalkyl and fluoroalkyl, or $R^4$ and $R^5$ taken together represent double-bonded oxygen, $R^6$ and $R^7$ taken together form a carbon—carbon double bond, $R^8$ may be H or $CH_3$, and wherein n is an integer having a value of from 1 to 5, and wherein the carbon at any one of positions 20, 22, or 23 in the side chain may be replaced by an O, S, or N atom.

9. The method of claim 8 wherein the symptoms are paralytic symptoms.

10. The method of claim 8 wherein the compound is selected from the group of 1,25-dihydroxyvitamin $D_3$, 19-nor-1,25-dihydroxyvitamin $D_2$, 19-nor-21-epi-1,25-dihydroxyvitamin $D_3$, 1,25-dihydroxy-24-homo-22-dehydro-22E-vitamin $D_3$, and 19-nor-1,25-dihydroxy-24-homo-22-dehydro-22E-vitamin $D_3$.

11. The method of claim 8 wherein the amount of compound administered is between 0.5 and 50 µg per day per 160 pound patient.

12. The method of claim 8 wherein the amount of compound administered is between 0.5 and 0.75 µg per day per 160 pound patient.

13. The method of claim 8 wherein the amount of compound administered is between 3.0 and 10 µg per day per 160 pound patient.

14. The method of claim 8 wherein the dose is given orally.

15. The method of claim 8 wherein the patient is on a low calcium diet.

16. The method of claim 8 wherein the administering is at night.

17. A method of delaying the onset or reducing the multiple sclerosis symptoms of an individual with a suspected risk of multiple sclerosis comprising administrating to the individual an amount of a vitamin D compound effective to delay or reduce symptoms and observing a delay or reduction in symptoms.

18. The method of claim 17 wherein the compound is 1,25(OH)$_2$D$_3$.

19. A method of delaying the onset or reducing the multiple sclerosis symptoms of an individual with a suspected risk of multiple sclerosis comprising the steps of administering to the individual an effective amount of the following compound:

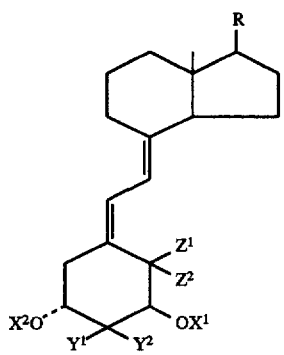

wherein $X^1$ and $X^2$ are each selected from the group consisting of hydrogen and acyl;

wherein $Y^1$ and $Y^2$ can be H, or one can be O-aryl or O-alkyl and can have a β or α configuration; $Z^1=Z^2=H$ or $Z^1$ and $Z^2$ together are $CH_2$; and wherein R is an alkyl, hydroxyalkyl or fluoroalkyl group, or R may represent the following side chain:

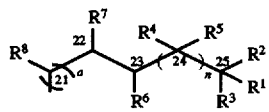

wherein (a) may have an S or R configuration, $R^1$ represents hydrogen, hydroxy or O-acyl, $R^2$ and $R^3$ are each selected from the group consisting of alkyl, hydroxyalkyl and fluoroalkyl, or, when taken together represent the group—$(CH_2)_m$—where m is an integer having a value of from 2 to 5, $R^4$ is selected from the group consisting of hydrogen, hydroxy, fluorine, O-acyl, alkyl, hydroxyalkyl and fluoroalkyl, $R^5$ is selected from the group consisting of hydrogen, hydroxy, fluorine, alkyl, hydroxyalkyl and fluoroalkyl, or $R^4$ and $R^5$ taken together represent double-bonded oxygen, $R^6$ and $R^7$ taken together form a carbon—carbon double bond, $R^8$ may be H or $CH_3$, and wherein n is an integer having a value of from 1 to 5, and wherein the carbon at any one of positions 20, 22, or 23 in the side chain may be replaced by an O, S, or N atom.

20. The method of claim 19 wherein the compound is selected from the group of 1,25-dihydroxyvitamin $D_3$, 19-nor-1,25-dihydroxyvitamin $D_2$, 19-nor-21-epi-1,25-dihydroxyvitamin $D_3$, 1,25-dihydroxy-24-homo-22-dehydro-22E-vitamin $D_3$, and 19-nor-1,25-dihydroxy-24-homo-22-dehydro-22E-vitamin $D_3$.

* * * * *